US00PP19363P3

(12) United States Plant Patent
Zaiger et al.

(10) Patent No.: US PP19,363 P3
(45) Date of Patent: Oct. 21, 2008

(54) NECTARINE PLANT NAMED 'HONEY MAY'

(50) Latin Name: *Prunus persica var. nucipersica*
Varietal Denomination: Nemaguard

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 324 days.

(21) Appl. No.: 11/374,566

(22) Filed: Mar. 14, 2006

(65) Prior Publication Data

US 2007/0220639 P1 Sep. 20, 2007

(51) Int. Cl.
*A01H 5/00* (2006.01)

(52) U.S. Cl. ..... Plt./190

(58) Field of Classification Search ..... Plt./190
See application file for complete search history.

*Primary Examiner*—Kent L. Bell
*Assistant Examiner*—Georgia Helmer

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous and upright tree growth.
2. Fruit ripening in the early maturity season.
3. Producing firm, yellow flesh fruit with very good flavor and eating quality.
4. Having a low winter chilling requirement of approximately 200 hours at or below 45° F.
5. Fruit holding firm on the tree 8–10 days after maturity.
6. Heavy and regular bearer of large size fruit.

1 Drawing Sheet

Botanical classification: *Prunus persica* var. *nucipersica.*

BACKGROUND OF THE VARIETY

Field of Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarines and peaches, which are known to us, and mentioned herein, 'May Glo' Nectarine (U.S. Plant Pat. No. 5,245), 'Tasty Gold' Nectarine (U.S. Plant Pat. No. 5,623), 'Royal Glo' Nectarine (U.S. Plant Pat. No. 8,281), 'May Crest' Peach (U.S. Plant Pat. No. 4,064), 'May Grand' Nectarine (U.S. Plant Pat. No. 2,794), 'Early Sun Grand' Nectarine (U.S. Plant Pat. No. 1,420), 'Royal Gold' Peach (U.S. Plant Pat. No. 2,663), 'Ruby Gold' Nectarine (U.S. Plant Pat. No. 3,101), 'Sunred' Nectarine (non-patented), 'June Glo' Nectarine (U.S. Plant Pat. No. 5,228), 'Desert Gold' Peach (non-patented) and the proprietary selections '55G815' and '43G1018'.

ORIGIN OF THE VARIETY

The new and distinct nectarine tree (*Prunus persica* var. *nucipersica*) was originated by us in our experimental orchard from seed of a first generation cross between selected proprietary parents with field identification numbers '212LK80' and '7LL208'. The seed parent (212LK80) originated from crosses between 'May Glo' Nectarine (U.S. Plant Pat. No. 5,245), 'Tasty Gold' Nectarine (U.S. Plant Pat. No. 5,623), 'Royal Glo' Nectarine (U.S. Plant Pat. No. 8,281), 'May Crest' Peach (U.S. Plant Pat. No. 4,064) and the proprietary selections '55G815' and '43G1018'. The pollen parent (7LL208) originated from crosses between the following varieties; 'May Grand' Nectarine (U.S. Plant Pat. No. 2,794), 'Early Sun Grand' Nectarine (U.S. Plant Pat. No. 1,420), 'Royal Gold' Peach (U.S. Plant Pat. 2,663), 'May Glo' Nectarine (U.S. Plant Pat. No. 5,245), 'Ruby Gold' Nectarine (U.S. Plant Pat. No. 3,101), 'Sunred' Nectarine (non-patented), 'June Glo' Nectarine (U.S. Plant Pat. No. 5,228), 'Desert Gold' Peach (non-patented) and 'May Crest' Peach (U.S. Plant Pat. No. 4,064). A large number of seed from this first generation cross of the proprietary parents '212LK80' and '7LL208' (both nectarines), were grown on their own root in our green house and these seedlings were budded to older trees of 'Nemaguard' Rootstock (non-patented) growing in our experimental orchard, located near Modesto, Calif., Stanislaus Country, to accelerate rapid fruit production for evaluation. Under close and careful observation of these budded seedlings we recognized the desirable fruit characteristics of the present nectarine variety and selected it in 2001 additional asexual propagation and commercialization.

ASEXUAL REPRODUCTION OF THE VARIETY

Additional asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree (*Prunus persica* var. *nucipersica*) is of large size, vigorous, upright growth and a productive, regular bearer of large, firm, yellow fleshed fruit with very good flavor and eating quality. The fruit is further characterized by ripening in the early maturity season, having an attractive red skin color, with good handling and shipping quality, the flesh being moderately juicy with a mild, sweet, low acid flavor. The tree having a relatively low winter chilling requirement of approximately 200 hours at or below 45° F. In comparison to its maternal parent (212LK80), the new variety requires approximately 50 hours less winter chilling and is approximately 20 days earlier in maturity. In comparison to its paternal parent (7LL208) the fruit of the new variety ripens in the same maturity season with larger size and requires approximately 50 hours more winter chilling.

PHOTOGRAPH OF THE VARIETY

The accompanying color photographic illustration shows typical specimens of the foliage and fruit with a flower inset of the present new nectarine variety at 5 years of age. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) and the colors are as nearly true as is reasonably possible in a color representation of this type. The additional photographic illustration shows typical flower buds and flowers of the present new nectarine variety at five years of age.

DESCRIPTION OF THE VARIETY

The following is a detailed botanical description of the new variety of nectarine tree, its flowers, foliage and fruit, as based on observations of 5 year old specimens grown near Modesto, Calif., with color in accordance with Munsell Book of Color.

Tree:

*Size.*—Large, normal for most varieties of nectarine trees. Pruned to 3 to 3.5 meters in height for economical harvesting of fruit. Average spread 3 to 3.5 meters, varies with different cultural practices.

*Vigor.*—Vigorous, growth of 1.5 to 2 meters the first growing season, varies slightly with fertility, type of soil and climatic conditions.

*Form.*—Upright, usually pruned to vase shape.

*Branching habit.*—Upright, crotch angle approximately 35°, increases with heavy crop load.

*Productivity.*—Productive. Normal fruit thinning and spacing necessary to develop desired market size fruit. Fruit set varies with climatic conditions during bloom time.

*Bearer.*—Regular, adequate fruit set 4 consecutive years. No alternate bearing observed.

*Fertility.*—Self fertile.

*Density.*—Medium dense. Pruning to open center of tree to vase shape desirable to enhance fruit color and keep fruit wood healthy.

*Hardiness.*—Hardy in all stone fruit growing areas of California. Winter chilling requirement approximately 200 hours at or below 45° F. Grown in USDA Hardiness Zone 9.

Trunk:

*Size.*—Medium to large. Average 53.3 cm in circumference at 21.6 cm above ground on a 5 year old tree.

*Stocky.*—Medium stocky.

*Texture.*—Medium shaggy, roughness increases with age of tree.

*Color.*—Varies from 10YR 4/4 to 2.5Y 5/2.

Branches:

*Size.*—Medium. Average circumference 15.5 cm at 1.3 meters above ground.

*Surface texture.*—New growth smooth, becomes rough with age.

*Lenticels.*—Average number 44 in a 25.8 sq cm area. Average length 3.6 mm. Average width 1.6 mm. Color varies from 7.5YR 6/6 to 7.5YR 5/6.

*Color.*—New growth varies from 2.5GY 6/6 to 5GY 6/6. Old growth varies from 10YR 4/2 to 10YR 3/4, varies with age of growth.

Leaves:

*Size.*—Large. Average length 151.8 mm. Average width 46.5 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins. Lower surface relatively smooth with small ridges created by midrib and pinnate venation. Both surfaces glabrous.

*Petiole.*—Medium. Average length 8.5 mm. Average width 1.6 mm. Surface glabrous. Longitudinally grooved. Color varies from 2.5GY 6/6 to 5GY 6/6.

*Glands.*—Reniform. Size — medium to large. Average length 1.2 mm. Average diameter 0.8 mm. Number varies from 1 to 5, average number 2. Located primarily on base of leaf blade and upper portion of the petiole. Color varies from 2.5GY 7/6 to 2.5GY 6/6.

*Color.*—Upper surface varies from 5GY 4/6 to 5GY 3/6. Lower surface varies from 5GY 5/4 to 5GY 4/6. Midvein color varies from 2.5GY 8/4 to 2.5GY 7/6.

Flower buds:

*Size.*—Medium. Average length 14.5 mm. Average diameter 8.0 mm.

*Hardiness.*—Hardy in all stone fruit growing areas of California.

*Form.*—Plump, conical, becoming elongated before opening.

*Pedicel.*—Average length 4.7 mm. Average width 0.7 mm. Color varies from 2.5GY 5/8 to 5GY 5/6.

*Color.*—Color varies from 5RP 8/6 to 5RP 7/10.

Flowers:

*Blooming period.*—Date of First Bloom Feb. 2, 2005. Date of Petal Fall Feb. 14, 2005, varies slightly with climatic conditions.

*Size.*—Large, showy. Average height 20.5 mm. Average diameter 37.0 mm.

*Petals.*—Number 5, alternately arranged to sepals. Orbicular, apex rounded, base narrows at point of attachment. Average length 19.5 mm. Average width 17.4 mm. Margin — sinuate, slightly cupped. Upper and lower surfaces glabrous. Color varies from 5RP 8/6 to 5RP 9/2, fades with age of flower.

*Sepals.*—Number 5, alternately arranged to petals. Shape — ovate, apex rounded. Size — medium. Average length 5.3 mm. Average width 4.7 mm. Upper surface glabrous. Lower surface pubescent. Color — upper surface varies from 2.5GY to 5GY 5/6. Lower surface varies from 7.5RP 3/4 to 7.5RP 3/6.

*Stamens.*—Average number 41 per flower. Average filament length 14.4 mm. Filament color varies from N 9.5/ (white) to 5RP 7/6. Anther color varies from 10R 4/8 around outer surface to 5Y 8/8 near the center of the anther.

*Pollen.*—Abundant, self fertile. Color varies from 5Y 8/8 to 5Y 7/8.

*Pistil.*—Number — normally 1, varies from 1 to 2. Surface — glabrous. Average length 18.7 mm. Position of stigma — same height as anthers. Color varies from 2.5GY 9/6 to 2.5GY 8/6.

*Fragrance.*—Slight.

*Pedicel.*—Average length 5.2 mm. Average width 0.8 mm. Color varies from 2.5GY 5/6 to 5GY 4/6.

*Color.*—Varies from 5RP 7/6 to 5RP 8/6.

*Number flowers per flower bud.*—Normally one.

Fruit:

*Maturity when described.*—Firm ripe.

*Date of first picking.*—May 1, 2005.

*Date of last picking.*—May 7, 2005, varies slightly with climatic conditions.

*Size.*—Large. Average diameter axially 57.4 mm. Average transversely in suture plane 64.2 mm. Average weight 133.5 grams, varies slightly with fertility of the soil, amount of thinning and climatic conditions.

*Form.*—Globose.

*Suture.*—Shallow, extends from base to apex.

*Ventral surface.*—Nearly smooth to very slightly lipped.

*Apex.*—Rounded to slightly retuse.

*Base.*—Rounded to slightly retuse.

*Cavity.*—Rounded to slightly elongated in suture plane. Average depth 5.1 mm. Average diameter 12.4 mm.

Stem:

*Size.*—Small. Average length 7.5 mm. Average diameter 3.3 mm.

*Color.*—Varies from 2.5GY 5/6 to 5GY 5/8.

Flesh:

*Ripens.*—Evenly.

*Texture.*—Firm, holds firm on the tree 8 to 10 days after maturity, shipping ripe.

*Fibers.*—Few, small, tender.

*Firmness.*—Firm, holds firm longer than most early maturing standard varieties.

*Aroma.*—Slight to moderate.

*Amydgalin.*—Undetected.

*Eating quality.*—Very good.

*Flavor.*—Very good, good balance between sugar and acid.

*Juice.*—Moderate amount, enhances flavor.

*Brix.*—Average 10.4°, varies slightly with amount of fruit per tree and climatic conditions.

*Color.*—Varies from 2.5Y 8.5/8 to 2.5Y 8/10. Pit cavity varies from 10YR 8/8 to 10YR 7/8.

Skin:

*Thickness.*—Medium.

*Surface.*—Smooth.

*Down.*—Wanting.

*Tendency to crack.*—None.

*Color.*—Ground color varies from 2.5Y 8.5/6 to 2.5Y 8/8. Overspread with 7.5R 3/10 to 7.5R 2/8 on approximately 90% of fruit surface.

*Tenacity.*—Tenacious to flesh.

*Astringency.*—None.

Stone:

*Type.*—Clingstone.

*Size.*—Large. Average length 30.3 mm. Average width 25.4 mm. Average thickness 20.1 mm.

*Form.*—Ovoid.

*Base.*—Usually flat, varies from flat to slightly rounded.

*Apex.*—Slightly pointed. Average length 0.4 mm.

*Surface.*—Pitted throughout, pits vary from rounded to slightly elongated. Ridges extend from base toward apex.

*Sides.*—Unequal, one side slightly larger, extending further form suture plane.

*Ridges.*—Relatively smooth with wide surface.

*Tendency to split.*—Very slight.

*Color.*—Varies from 7.5YR 6/8 to 7.5YR 5/6 when dry.

Kernel:

*Form.*—Ovate.

*Taste.*—Bitter.

*Viability.*—Poor, embryo only partially developed.

*Size.*—Large. Average length 17.2 mm. Average width 13.2 mm. Average depth 6.3 mm.

*Skin.*—Color varies from 2.5Y 8.5/2 to 2.5Y 8.5/4 when dry.

Use: Dessert. Market — local and long distance.

Keeping quality: Good, held firm in cold storage at 38° to 42° F. for 2 weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree, substantially as illustrated and described.

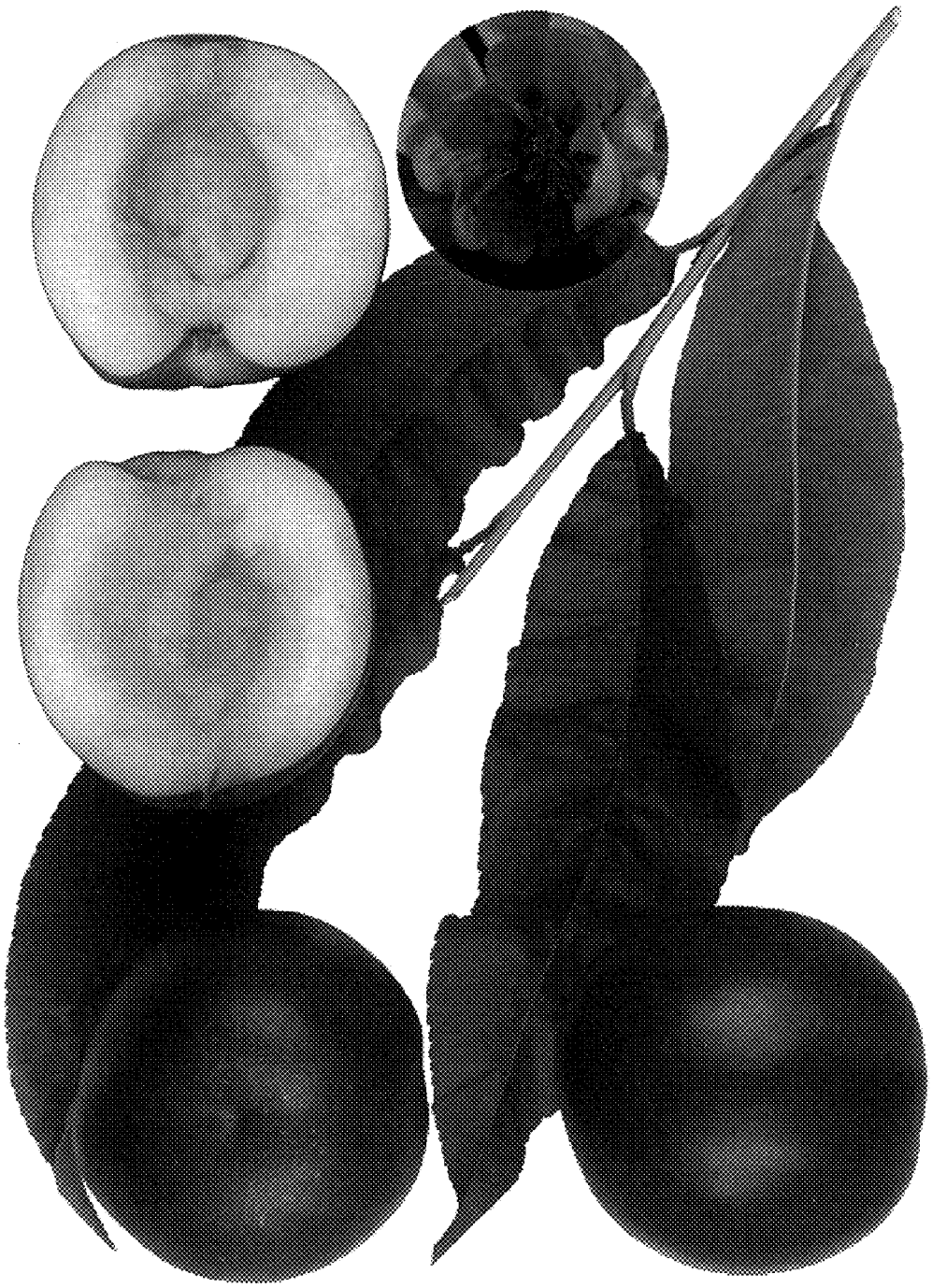

* * * * *